United States Patent [19]
Ruggiero et al.

[11] Patent Number: 5,762,650
[45] Date of Patent: Jun. 9, 1998

[54] BIOCIDE PLUS SURFACTANT FOR PROTECTING CARPETS

[75] Inventors: Murray A. Ruggiero, East Haven, Conn.; Phil Magan, Marietta, Ga.; Thomas Edgar Robitaille, Rising Sun, Md.; Robert P. Roth, Cheshire; James J. Irovando, Meriden, both of Conn.

[73] Assignee: Olin Corporation, Cheshire, Conn.

[21] Appl. No.: 701,822

[22] Filed: Aug. 23, 1996

[51] Int. Cl.$^6$ .................................................. D06P 5/00
[52] U.S. Cl. ...................... 8/490; 8/565; 8/567; 8/568; 8/587; 8/588; 8/589; 8/590; 8/602; 8/610
[58] Field of Search ...................... 8/490, 565, 567, 8/568, 588, 589, 590, 602, 610, 611; 106/15.05; 252/8.61, 8.81

[56] References Cited

U.S. PATENT DOCUMENTS

| | | | |
|---|---|---|---|
| 2,742,476 | 4/1956 | Bernstein et al. | 260/294.8 |
| 2,809,971 | 10/1957 | Bernstein et al. | 260/270 |
| 3,264,242 | 8/1966 | Teot | 260/29.6 |
| 3,592,584 | 7/1971 | Link et al. | 8/26 |
| 3,634,272 | 1/1972 | Valenta et al. | 352/153 |
| 3,684,426 | 8/1972 | Bindler et al. | 8/15 |
| 3,818,018 | 6/1974 | Weisse | 260/294.8 |
| 3,940,482 | 2/1976 | Grand | 424/245 |
| 3,945,437 | 3/1976 | Chiu et al. | 166/305 |
| 3,956,401 | 5/1976 | Scardera et al. | 260/615 |
| 4,401,770 | 8/1983 | Hance | 521/120 |
| 4,443,222 | 4/1984 | Morris et al. | 8/189 |
| 4,450,090 | 5/1984 | Kinney | 252/106 |
| 4,818,436 | 4/1989 | French et al. | 252/400 |
| 4,898,621 | 2/1990 | Prueha et al. | 134/25.2 |
| 4,925,587 | 5/1990 | Schenker et al. | 252/174.22 |
| 5,030,245 | 7/1991 | Hemling et al. | 8/560 |
| 5,100,655 | 3/1992 | Takano et al. | 424/63 |
| 5,360,457 | 11/1994 | Ruggiero et al. | 8/567 |
| 5,424,435 | 6/1995 | Hani et al. | 546/296 |
| 5,451,238 | 9/1995 | Ruggiero et al. | 8/567 |
| 5,460,632 | 10/1995 | Ruggiero et al. | 8/552 |
| 5,534,165 | 7/1996 | Pilosof et al. | 252/8.91 |

OTHER PUBLICATIONS

Tyrone L. Vigo, "*Antibacterial Finishing of Textiles*", CHEMTECH, Jul., 1976, pp. 455–458.

M.R. Porter, "*The Handbook of Surfactants*", Blackie & Son, limited no month available (1991), pp. 49–202.

*Primary Examiner*—Margaret Einsmann
*Attorney, Agent, or Firm*—Dale Lynn Carlson; Wiggin & Dana

[57] ABSTRACT

A composition and a process are disclosed for imparting durable antimicrobial properties to fibrous materials. The composition contains a leveling surfactant and a water-insoluble antimicrobial compound. In one embodiment, simultaneous dyeing and antimicrobial finishing of a fibrous material is achieved using an aqueous dye bath containing the aforesaid composition.

17 Claims, No Drawings

BIOCIDE PLUS SURFACTANT FOR PROTECTING CARPETS

FIELD OF THE INVENTION

This invention relates to an improvement in the art of finishing fibrous materials. More particularly, the invention relates to a composition and a process for imparting antimicrobial, and particularly antifungal, properties to textiles and other fiber-based materials.

BACKGROUND OF THE INVENTION

It is generally well-known in the art that textiles and other fibrous materials can be treated with certain bactericidal agents in order to render them resistant to the harmful or undesirable effects of various organisms. For a review of problems and prospects in this field of technology, see Tyrone L. Vigo, *Antibacterial Finishing of Textiles*, CHEMTECH, Jul. 1976, pp.455–458.

Prior art antimicrobial finishing of textiles has typically been less durable than otherwise might be desired, particularly in applications in which the textile is repeatedly exposed to the elements or subjected to multiple cleanings, e.g., in a laundering or shampooing, operation. This shortcoming, as it relates to the treatment of cellulosic textiles with one substantially water-insoluble, antimicrobial additive, namely zinc pyrithione, is addressed in U.S. Pat. No. 4,443,222, issued Apr. 17, 1984 to Morris et al. The '222 patent discloses a multi-step process for forming a wash-resistant deposit of zinc pyrithione on the textile. To this end, the textile is treated with an aqueous solution containing zinc pyrithione, a polyamine serving as a complexing agent to solubilize the zinc pyrithione, and urea. Following such treatment, the textile is heated to an elevated temperature to drive off the moisture and bring about a desired chemical reaction between the polyamine and the urea. The result of this reaction is said to be that carbamoyl groups are introduced into the polyamine molecule by way of the added urea, rendering the polyamine less effective as a complexing agent for the zinc pyrithione. As such, its solubilizing effect is reduced, thus producing a deposit of solid zinc pyrithione on the dried textile. This process of solubilizing and then insolubilizing the pyrithione results in wasted zinc pyrithione, an expensive chemical, since not all of the polyamine-solubilized pyrithione becomes insolubilized as desired, and requires the use of added urea, thus rendering the textile treating solution more complex than otherwise might be desired.

Simpler, more efficient processes for imparting durable antimicrobial properties to textiles using water-insoluble antimicrobial additives in urea-free treating solutions for carpets and other fibers would be highly desired by the carpet and textile manufacturing and finishing communities. The present invention provides one such process.

SUMMARY OF THE INVENTION

Now, in accordance with this invention, an improved composition has been found for imparting antimicrobial properties to fibers and fibrous materials, which comprises a select antimicrobial compound and a surfactant.

Further according to the invention, a simplified yet highly efficient process is provided for the antimicrobial finishing of textiles and other fibrous materials using the aforesaid composition. The process disclosed herein is advantageously adapted for effecting the dyeing and antimicrobial finishing of textiles simultaneously and in a very cost-effective way.

In one aspect, the present invention relates to a composition for the antimicrobial treatment of fibers and fibrous materials which comprises:

(a) a water insoluble antimicrobial compound selected from the group consisting of zinc pyrithione, copper pyrithione, ferrous pyrithione, ferric pyrithione, manganese pyrithione, nickel pyrithione, cobalt pyrithione, cadmium pyrithione, bismuth pyrithione, lead pyrithione, zirconium pyrithione, halopropynyl carbamates (e.g., 3-iodo-2-propynylbutyl carbamate, so-called "IPBC", or chloro- or bromo-substituted propynyl carbamates), 2,6-dichloro-N-octyl-isothiazalone, 2-octyl-3-isothiazalone, 1-hydroxy-6-substituted pyridiones having a 6-ring substituent selected from —O—R and —S—R, wherein O is oxygen, S is sulfur, and R is a substituted or unsubstituted hydrocarbon radical having between 1 and 20 carbon atoms, and combinations thereof, and (b) a leveling surfactant selected from the group consisting of alkali metal organosulfonates, alkaline earth metal organosulfonates, piperazine-substituted organosulfonates, piperazinone-substituted organosulfonates, and combinations thereof.

In another aspect, the present invention relates to a process for imparting antimicrobial properties to a fibrous material which comprises contacting the fibrous material with an aqueous formulation containing an antimicrobially effective amount of the above-describe composition.

In yet another aspect, the present invention relates to a composition for the antimicrobial treatment of fibers and fibrous materials which comprises:

(a) a zinc salt of a 1-hydroxy-2(1H)-pyridinethione compound represented by the formula

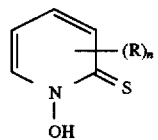

in which R is a member selected from the group consisting of hydrogen, lower alkyl, lower alkoxy and halogen, and (b) a leveling surfactant selected from the group consisting of alkali metal organosulfonates, alkaline earth metal organosulfonates, piperazine-substituted organosulfonates, piperazinone-substituted organosulfonates, and combinations thereof.

In still another aspect, the present invention relates to a process for simultaneously dyeing and antimicrobially treating a fibrous material which comprises dipping or spraying said fibrous material with an aqueous bath comprising:

(a) a water insoluble antimicrobial compound selected from the group consisting of zinc pyrithione, copper pyrithione, ferrous pyrithione, ferric pyrithione, manganese pyrithione, nickel pyrithione, cobalt pyrithione, cadmium pyrithione, bismuth pyrithione, lead pyrithione, zirconium pyrithione, halopropynyl carbamates (e.g., 3-iodo-2-propynylbutyl carbamate, so-called "IPBC", or chloro- or bromo-substituted propynyl carbamates), 2,6-dichloro-N-octyl-isothiazalone, 2-octyl-3-isothiazalone, 1-hydroxy-6-substituted pyridiones having a 6-ring substituent selected from —O—R and —S—R, wherein O is oxygen, S is sulfur, and R is a substituted or unsubstituted hydrocarbon radical having between 1 and 20 carbon atoms, and combinations thereof, (b) a leveling surfactant selected from the group consisting of alkali metal organosulfonates, alkaline earth metal organosulfonates, piperazine-substituted organosulfonates, piperazinone-substituted organosulfonates, and combinations thereof, and (c) an aqueous dye, to provide a dyed fibrous material exhibiting antimicrobial effectiveness against microbes. Yet another aspect of this invention relates to the dyed fibrous material product produced by this process.

These and other aspects will become apparent upon reading the following detailed description of the invention.

DETAILED DESCRIPTION OF THE INVENTION

It has now been surprisingly found in accordance a select combination of a water-insoluble antimicrobial compound and a leveling surfactant provides a composition is particularly useful as a (e.g., wool, silk or nylon fibers) to impart antimicrobial effectiveness to the fibrous material. This antimicrobial effectiveness entails durable resistance to attack by microbes, such as fungus, mildew, bacteria, algae, and the like. The leveling surfactant facilitates the level deposition of dye and/or antimicrobial compound onto the fibrous material substrate receiving this deposition.

This discovery, which seems to have eluded the skilled artisans in this field, makes it possible, in accordance with one aspect of the invention, to accomplish the dyeing and antimicrobial treatment of textiles simultaneously and economically. Since its implementation is very simple and requires no extra steps or special chemicals, this discovery makes possible improved efficiencies in the production of durable, antimicrobially-protected carpets and textiles.

Generally speaking, the antimicrobial compound useful in the composition of the present invention is one that, when combined with a surfactant as taught herein, imparts durable antimicrobial properties to fibers and other fibrous materials. The antimicrobial compounds useful in the present invention are "essentially water-insoluble", inasmuch as the water solubility of each of these compounds is less than 500 ppm at 20 degrees Centigrade. These antimicrobial compounds are typically employed as dispersions wherein the antimicrobial compound is suspended in an aqueous medium. Selectivity in choosing the antimicrobial compound, as well as combining it with a leveling surfactant, are important considerations within the scope of the present invention.

Illustrative antimicrobial compounds which may be employed in accordance with the invention are selected members of various groups of pyridinethione and related compounds, including the following groups:

(a) Heavy metal salts of 1-hydroxy-2(1H)-pyridinethione compounds of the formula

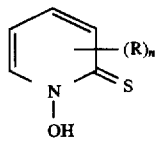

I in which R represents a member selected from the group consisting of hydrogen, lower alkyl, lower alkoxy and halogen and n is a positive integer less than 5.

(b) 2,2'-Dithiobis-pyridine-1,1'-dioxide and adducts thereof which are represented by the formula

(C₃H₄NOS)₂MY

II wherein M is an alkaline earth metal, Y is an anion selected from the group consisting halide, sulfate, nitrate chlorate and acetate, and t is 1 or 2; and (c) 1-Hydroxy-6-substituted-2-pyridones represented by the formula

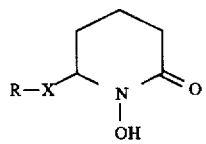

III wherein X is oxygen or sulfur and R is a substituted or unsubstituted hydrocarbon radical having from 1 to 20 carbon atoms.

All of the foregoing compounds and groups of compounds, and their preparation, are well-known in the art. Thus certain heavy metal salts of the 1-hydroxy-2(1H)-pyridinethione compounds of group (a) above are described in U.S. Pat. No. 2,809,971, issued Oct. 15, 1957 Aug. 17, 1954 to Bernstein et al. Another Bernstein et al. patent, U.S. Pat. No. 2,742,476, issued Apr. 17, 1956, describes the preparation of 2,2'-dithiobis-pyridine-1,1'-dioxide; and its adducts represented by formula II above are described in U.S. Pat. No. 3,818,018, issued Jun. 18, 1974 to Weisse et al. Finally, the 1-hydroxy-6-substituted-2-pyridones of group (c) above are described in U.S. Pat. No. 5,424,435, issued Jun. 13, 1995 to Hani et al. The entire disclosures of all of the foregoing patents are incorporated herein by reference.

The preferred antimicrobial compounds for use herein are the heavy metal salts of 1-hydroxy-2(1H)-pyridinethione of group (a) above, particularly the zinc salt (i.e., zinc pyrithione), the copper salt (i.e., copper pyrithione) and mixtures thereof. Zinc pyrithione is the most preferred bactericide. In accordance with one economically advantageous embodiment of the invention for using zinc pyrithione as the bactericide of choice, this salt is suitably formed in-situ by transchelation from a precursor mixture of the sodium pyrithione and a water-soluble zinc salt, e.g., a salt of a mineral acid such as zinc sulfate.

The antimicrobial compound is used in any suitable proportion that is effective in achieving a desired level of antimicrobial activity. Obviously, for economic and environmental reasons, one would want to use the minimum amount necessary. As discussed in more detail below, the necessary or required level of bactericide may vary substantially depending on a number of factors including the identity and efficacy of the particular bactericide and the level of antimicrobial property desired depending on the product being treated. Thus as used herein with reference to the antimicrobial compound, the term "effective amount" or "antimicrobially effective amount" is intended to mean and include any proportion, the use of which achieves the desired antimicrobial result or effect in the fibrous material which is to be treated in accordance with the invention. Typically, the antimicrobial compound is incorporated in an aqueous bath or medium which is used to treat the fibrous material, the concentration of the bactericide ranging for example from about 0.001 to about 10 percent by weight based on the weight of the aqueous bath. A preferred proportion range, where the bactericide is zinc pyrithione for example, is from about 0.005 to about 5.0, and optimally about 0.01 to about 3.0, percent by weight.

A surfactant is the second component used to prepare the composition of the invention. It has been found that the antimicrobial treatment of fibrous materials in the presence of a surfactant, as used for example in conjunction with the dyeing of textiles, not only facilitates the treatment, particularly where the biocide used is water-insoluble, but also results in a more durable antimicrobial property being imparted to the fibrous material. Any surfactant, be it a monomeric or polymeric material, may be used including anionic, cationic and nonionic surfactants. Numerous varieties of such materials are well-known in the art, many of them being available commercially. For a general description of a wide range of surfactants, see for example, M. R. Porter, *The Handbook of Surfactants*, Blackie & Son, limited (1991), pp 49–202. See also U.S. Pat. Nos. 4,898,621, 4,925,587, 3,956,401, and 5,030,245. The entire disclosures of the foregoing handbook and patents are incorporated herein by reference. Generally, surfactants that exhibit at least some dye leveling activity are preferred for use according to the invention; and the term "leveling surfactant", as used herein, is intended to mean and include any and all such surfactants.

Leveling surfactants for use herein include those comprising one or more members of the group consisting of (a) the organosulfonates (including substituted and unsubstituted mono and polyfunctional materials), (b) the alcohol alkoxylates, (c) the organic and inorganic salts of polycarboxylated alcohol alkoxylates and mixtures thereof.

Illustrative organosulfonate leveling surfactants include the aralkyl ether sulfonates, such as those represented by formula VI below and, more specifically, the commercially available alkyl diphenyl oxide disulfonates (available for example under the trademark DOWFAX 2A1), disodiumdodecyl-diphenylether disulfonate, the piperazine-, piperazinone- or amine-substituted organo-sulfonates and mixtures thereof. For more information concerning the alkyl diphenyl oxide sulfonates and their preparation, see for example U.S. Pat. Nos. 3,264,242; 3,634,272; and 3,945, 437, the entire disclosures of which are incorporated herein by reference.

As for the alcohol alkoxylates, U.S. Pat. No. 3,956,401, which is also incorporated herein by reference in its entirety, discloses a wide variety of such compounds. Illustrative such materials can be represented by the formula

wherein $R^4$ is a linear, alkyl radical having an average of about 7 to about 10 carbon atoms, each of $R^5$ and $R^6$ is independently a linear alkyl radical having about 1 to 4 carbon atoms, d is an integer of about 1 to 6, e is an integer of about 4 to 15 and f is an integer of about 4 to 25.

Several alcohol alkoxylates are available commercially, which can be used in practicing the invention. These include for example various linear alcohol alkoxylate products of Olin Corporation sold under the trademark POLY-TERGENT, namely, POLY-TERGENT SL-42 and propylene end-capped POLY-TERGENT SLF-18. These and other alkoxylates are described in U.S. Pat. Nos. 4,898,621 and 4,925,587, both of which patents are incorporated herein by reference. Another commercial product is a Union Carbide nonionic surfactant sold under the trademark TERGITOL XL-80N, which is a mixture of ethoxylated and propoxylated primary alcohols having an average molecular weight of approximately 420. Still another commercially available nonionic alcohol alkoxylate is a Shell Chemical product sold under the trademark NEODOL 91-6.

Turning now to the third category of surfactants mentioned above, namely, the organic and inorganic salts of polycarboxylated alcohol alkoxylates, these can be salts of polycarboxylated linear, branched or cyclic alcohol alkoxylates and mixtures thereof. Illustrative polycarboxylated alcohol alkoxylates include those represented by the formula

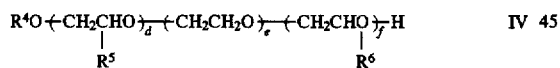

in which R is a hydrocarbon radical having about 6 to about 18 carbon atoms, R' is hydrogen or a hydrocarbon radical having 1 to 8 carbon atoms, f is a number from 1 to 25 and each of X and Y is independently selected from the group consisting of hydrogen, methyl and succinic acid radicals, with the proviso that at least one X or Y is a succinic acid radical. Any of a wide variety of inorganic and organic bases may be used to neutralize at least a portion of the acid groups on the polycarboxylated alcohol alkoxylate to provide the desired salt thereof, such as an alkali metal hydroxide, and alkaline earth metal hydroxide, ammonium hydroxide, mon-, di- or tri-ethanolamine, mixtures thereof and the like. Typically, in making the salt, at least one mole of the inorganic or organic base is employed per mole of the polycarboxylated alcohol alkoxylate. For economic and practical reasons, the most preferred salts are the sodium salts of polycarboxylated alcohol alkoxylates.

A particularly effective group of leveling surfactants for use in accordance with the invention is that comprising a piperazine-, piperazinone- or amine-substituted organosulfonate and mixtures thereof. For a detailed description of these materials and their preparation, see U.S. Pat. No. 5,451,238, issued Sep. 19, 1995 to Ruggiero et al. and U.S. Pat. No. 5,360,457, issued Nov. 1, 1994 to Ruggiero et al., the entire disclosures of which are incorporated herein by reference.

The aforesaid substituted oraganosulfonates are the products of reacting, for example, a piperazine compound, a piperazinone compound, an amine compound or a mixture thereof with an aralkyl ether sulfonate compound, using a molar ratio of sulfonate compound to piperazine, piperazinone or amine compound ranging from about 10:1 to about 1:10, preferably about 2:1 to about 1:2. Preferred piperazine compounds are those selected from the group consisting of anhydrous piperazine, 1,2-aminoethyl piperazine, 1,4-piperazine-diethane sulfonic acid, hydrated piperazine and combinations thereof. Preferred piperazinone compounds are the 2-piperazinones, particularly 4-(2-hydroxyethyl)-2-piperzinone, N,N-dimethyl-2-piperazinone and mixtures thereof. As for the amine compounds, particularly preferred such materials are those selected from the group consisting of monoethanolamine, triethanolamine, ammonium hydroxide and mixtures thereof. The piperazine compounds are particularly preferred.

The other reactant used in preparing the aforesaid substituted organosulfonate surfactants can be any suitable organosulfonate. However, it is preferable to use an aryl ether sulfonate as discussed hereinabove, illustrative of which are the alkylated diphenyl oxide sulfonates having at least one alkyl substituent on a phenyl ring, which substituent may be linear, branched or cyclic. Particularly preferred are the diphenyl oxide sulfonate anionic surfactants, including mixtures of two or more such surfactants. These particular surfactants may be represented by the following formula

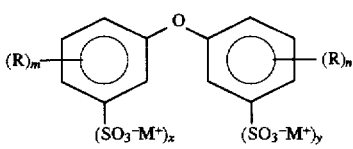

wherein each R is independently a substituted or unsubstituted aliphatic radical; each of m and n is independently 0, 1 or 2; each M is independently hydrogen, an alkali metal, an alkaline earth metal, ammonium or substituted ammonium; and each of x and y is independently 0 or 1. Preferably, each R is independently an alkyl group having from 8 to 24, more preferably from 10 to 20 and optimally 16, carbon atoms. Each such alkyl group can be linear, branched or cyclic, the non-cyclic radicals (i.e., linear or branched) being preferred. The M+ammonium or substituted ammonium ion is represented by the formula $$(R')_3NH+ \qquad\qquad VII$$

in which each R' is independently hydrogen, an alkyl group having 1 to 4 carbon atoms or a hydroxyalkyl group having 1 to 4 carbon atoms. In accordance with an especially preferred embodiment of the invention, each M in formula VI above is hydrogen, sodium, potassium, calcium or ammonium.

In certain applications, it is advantageous to employ a surfactant composition comprising an organosulfonate, especially a piperazine-, piperazinone- or amine-substituted organosulfonate. Preferably one or more diluents or surfactant supplements are added. This approach is particularly preferred for example in those embodiments of the invention wherein the composition disclosed herein is to be used in an operation involving the simultaneous antimicrobial treatment and dyeing of a textile or other fibrous material. A particularly effective such diluent for this purpose is an alcohol alkoxylate. This can be selected from a large variety of such compounds as described hereinabove. In accordance with a further preferred embodiment of the invention, the surfactant component is comprised of the aforesaid substituted organosulfonate, an alcohol alkoxylate and an organic or inorganic salt of a polycarboxylated alcohol alkoxylate, the latter as described above and in the aforesaid U.S. Pat. No. 5,369,457 to Ruggiero et al.

In those embodiments where the surfactant component of the composition of the invention is a combination of a substituted organosulfonate and an alcohol alkoxylate, it is preferable to employ a weight ratio, of organosulfonate to alkoxylate, from about 40:60 to about 88:12; and where a third ingredient, namely, a salt of a polycarboxylated alcohol alkoxylate, is included in the surfactant component, it is preferable to use an amount of the salt which is equivalent to from about 2 to about 50 percent of the weight of the organosulfonate.

The surfactant component of the composition of the invention may be used in any suitable proportion which is effective in promoting the antimicrobial treatment (by the bactericide component) of the fibrous material. Thus here again the term "effective proportion"as used in relation to the surfactant is intended to mean any such proportion or amount sufficient to effect deposit of the antimicrobial compound onto the fibrous material being treated while preparing the fibrous material for simultaneous or subsequent dyeing thereof. Usually the proportion of surfactant required coincides with the amount needed to effect dye leveling of the fibrous material, such as generally from about 0.05 to about 35 percent, and preferably from about 1 to about 25 percent, by weight of the aqueous bath.

As stated hereinabove, each of the two essential components of the composition of the invention (i.e., the antimicrobial compound and the surfactant) is used in a proportion which is effective in fulfilling the function of that component as an ingredient of the aqueous bath in which the fibrous material is to be treated. Otherwise, there is no criticality with respect to the proportions of the antimicrobial component and the surfactant component relative to one another. Thus any weight combination of biocide and surfactant which is effective, in an aqueous bath, to impart durable antimicrobial properties to a fibrous material, may be employed within the broad parameters of this invention. Such combination my vary widely depending on a variety of factors including, for example, the make-up or composition of the aqueous bath, the level of antimicrobial properties desired (which in turn depends on the type of end-use that the fibrous material will be put to), the nature and efficacy of each of the particular biocide and surfactant, the type of fibrous material to be treated, and so forth.

Also as noted earlier, the composition of the invention is designed for use in an aqueous formulation or bath with which the fibrous material is to be treated. As such, the composition may be prepared in the desired, final level of concentration in an aqueous medium ready for treating the fibrous material; or, it can be prepared in a more concentrated form, to be added to the treatment bath in such amount as to achieve the required or desired final concentration.

In addition to the two main components of the composition of the invention, other ingredients may be included, if desired or necessary, to achieve a specific result or function. This includes for example defoamers, pH control agents, solubilizing agents, colorants, emulsifiers and so forth, provided of course that such additives have no detrimental effect on the fibrous material or the antimicrobial properties sought to be imparted to it.

In accordance with the method of the invention, all types of fibers and fiber-based materials can be treated with the composition disclosed herein. Thus the fibers can be natural or synthetic fibers such as cotton, wool, silk, polyester, polyamide, and so forth. Synthetic fibers and fiber-based materials are preferred inasmuch as they are particularly suited for treatment with the composition of the invention, the polyamides being most preferred. Suitable synthetic fiber materials which are made from polyamide include for example the condensation products of hexamethylenediamine and adipic acid (Polyamide 6.6) or sebacic acid (Polyamide 6.10), or mixed condensation products, such as derived from hexamethylenediamine, adipic acid and E-caprolactam (Polyamide 6.6/6), and so forth. In accordance with a one practical embodiment, the process of the invention is advantageously used for the antimicrobial treatment of carpets, particularly those made of nylon fibers.

The process of the invention comprises contacting the fibrous material with an aqueous medium containing the bactericide and the surfactant. As used herein, the term "fibrous material" or "fiber-based material" is intended to mean and include any material which is made partly or wholly from fibers, including woven and non-woven materials such as various textiles and fabrics, fiber bat materials, and so forth. Any suitable means or procedure for effecting such contact may be employed. Typically, the treatment is carried out in an aqueous bath to which the desired amounts of biocide and surfactant have been added. Preferably, the bath is then agitated or stirred to achieve a substantially homogenous consistency. It is also preferable to control the pH of the bath within a range from about 3.5 to about 9 and more preferably from about 5 to about 7. Any suitable materials may be used for adjusting (i.e., raising or lowering) the pH, such as sodium carbonate and acetic acid; and ammonium sulfate may be employed to maintain the pH at the desired level. Following preparation of the aqueous bath and adjustment of its pH, the fibrous material is placed and soaked therein for a sufficient amount of time to permit complete penetration of the fibers. Preferably, the treatment is carried out while maintaining the bath at elevated temperatures, most preferably at about boiling temperature (e.g., about 95°–105° C.) It is also preferable to effect the raising of the temperature of the bath gradually, such as by applying heat sufficient to raise the bath temperature at the rate of about 1° C. per minute. After soaking in the hot bath for a duration sufficient to ensure complete penetration of the fibers, such as for example from about 30 minutes to about 2 hours, the fibrous material is removed, rinsed with water and then dried.

In accordance with an especially advantageous embodiment of the invention, the antimicrobial treatment of a fibrous material is carried out simultaneously with the dyeing of such material. To this end, the desired dye, in an amount sufficient to effect the requisite or desired coloration of the fibers, is added to the antimicrobial composition disclosed herein, and then substantially the same procedure is followed as described above.

The economic advantages realized from using a single bath and a straight-forward, simple procedure, to effect the simultaneous dyeing and antimicrobial treatment of textiles and other fibrous materials, in accordance with this embodiment, cannot be overstated. The practice of this aspect of the invention is suitable for use with numerous dyes of various types, although it is particularly adapted for use when dyeing with acidic dyes or dispersed dyes, as described for example in the above cited U.S. Pat. No. 5,451,238 to Ruggiero et al.

The following examples are intended to illustrate, but in no way limit the scope of, the present invention. All patents cited in this application are incorporated by reference herein in their entirety. All percentages referred to herein are by weight, unless otherwise specified.

ILLUSTRATIVE EXAMPLES

The following examples are provided merely to illustrate the invention. In these examples, the tested fibrous material specimens are carpet swatches made of Nylon 6 fibers or Nylon 6.6 fibers, some pre-dyed and some undyed or natural color, as indicated. Two swatches ("a" and "b") are used in each example. Procedures prescribed by the American Association of Textile Chemists and Colorists (AATCC) are followed in performing the testing. More specifically, the bacterial inhibition test is in accordance with AATCC 174-1 using Staphylococcus Aureus as the test microorganism, and the procedure for washing the specimen fibrous material before it is retested for retention of bacterial inhibition is as set forth in AATCC 138-1987. The results of the bacterial inhibition test are reported as follows:

"GCA"—means growth was found in the contact area, i.e., no bacterial inhibition.

"NGCA"—means there was no growth found in the contact area, i.e., total inhibition in the contact area.

"NGCA+"—means total inhibition extended beyond the contact area for the indicated length in millimeters, on both sides, e.g., "NGCA+2.5" means that no growth was found not only in the contact area but extending 2.5 mms. beyond it on each side.

Finally, the bactericidal composition used to treat the carpet specimens is an aqueous bath adjusted to a pH of 6 and maintained at that pH by the addition 2 percent of ammonium sulfate. The composition contains 0.60 percent of zinc pyrithione, a commercial product available under the trademark "zinc OMADINE", and 2 percent of a surfactant. In Examples 1 through 6, that surfactant is a blend, available commercially under the trademark POLYTERGENT ADL ULTRA-A, of (a) 1,2-(aminoethyl) piperazine-substituted alkyl diphenylether disulfonate prepared in accordance with the procedure described in Example 1 of the above-cited U.S. Pat. No. 5,360,457 to Ruggiero et al., (b) polycarboxylated linear alcohol alkoxylate, a commercial product of Olin Corporation sold under the trademark POLYTERGENT CS-1, neutralized with 50% sodium hydroxide and (c) a linear alcohol alkoxylate which is another commercial product available under the trademark POLYTERGENT SL-42. And in Examples 7 and 8, the surfactant used is another commercial product, available under the trademark POLYTERGENT 2A1, which is an alkyl diphenylether disulfonate. For convenience and easy reference, the bactericides zinc pyrithione and sodium pyrithione are referred to hereinbelow as "Zn OMADINE" and "Na OMADINE", respectively, the surfactant blend is referred to as "ADL-ULTRA" and the POLYTERGENT 2A1 surfactant is referred to as "2A1". All parts and percentages are by weight unless otherwise specified.

EXAMPLE 1

Duplicate carpet specimens made of natural (undyed) Nylon 6 fibers were immersed in a bath of the bactericidal composition described above, and the bath was heated such as to raise its temperature at the rate of 1° C. per minute, until a temperature of 100° C. was reached. This temperature was maintained for 60 minutes. Thereafter the specimens were removed, rinsed with running water, allowed to air dry and then tested for bacterial inhibition. The results are reported in the Table below.

Comparison A

The procedure of Example 1 was followed except that the treatment bath did not contain any zinc OMADINE. The specimens did not exhibit any bacterial inhibition.

EXAMPLE 2

This example is an exact repetition of Example 1, and the results are provided in the Table below.

EXAMPLES 3 & 4

The procedure of Example 1 was followed except for the fact that the carpet swatches had been predyed red. The results of the inhibition tests are provided in the Table below.

Comparison B

The procedure of Example 1 was followed except that instead of zinc pyrithione, another commercial biocide was used at the same level, namely, sodium OMADINE antimicrobial (i.e., sodium pyrithione). As indicated in the Table, growth was found in the contact area. This comparison is provided to demonstrate the need for selectivity in choosing the right biocide or bactericide for use according to the invention. Thus although zinc pyrithione is effective, a closely related salt, sodium pyrithione, when tested at the same level of concentration, was found to be not effective.

EXAMPLE 5

The procedure of Example 1 was followed with one modification, namely, a dye formulation was added to the bath in order to (simultaneously with the antimicrobial treatment) dye the carpet swatches brown. The dye formulation consisted of 5.83 grams of blue dye, 5.83 grams of orange dye and 4.86 grams of red dye. One of two carpet specimens treated was tested for bacterial inhibition as per Example 1 (reported in the Table below as 5A). The other specimen (5B) was subjected to washing in accordance with AATCC 138-1987, and then tested for bacterial inhibition. The results of the bacterial inhibition tests for the unwashed and washed specimens are reported in the Table below.

EXAMPLE 6

The identical procedure of Example 5 was followed to treat two swatches of Nylon 6,6 carpeting. The results are tabulated below.

TABLE

| | Antimicrobial property Data | | |
|---|---|---|---|
| Example No. | Bactericide | Surfactant | Zone of Inhibition |
| 1 | Zn OMADINE ® (0.6%) | POLY-TERGENT ® ADL-ULTRA (2.0%) | a: NGCA + 3.5 mm b: NGCA + 2.5 mm |
| Comp. A | None | POLY-TERGENT ® ADL-ULTRA (2.0%) | a: GCA b: GCA |
| 2 | Zn OMADINE ® (0.6%) | POLY-TERGENT ® ADL-ULTRA (2.0%) | a: NGCA + 3.0 mm b: NGCA + 1 mm |
| 3 | Zn OMADINE ® (0.6%) | POLY-TERGENT ® ADL-ULTRA (2.0%) | a: NGCA b: NGCA + 3.5 mm |
| 4 | Zn OMADINE ® (0.6%) | POLY-TERGENT ® ADL-ULTRA (2.0%) | a: NGCA + 1 mm b: NGCA |
| Comp. B | Na OMADINE ® (0.6%) | POLY-TERGENT ® ADL-ULTRA (2.0%) | a: GCA b: GCA |
| 5A | Zn OMADINE ® (0.6%) | POLY-TERGENT ® ADL-ULTRA (2.0%) | NGCA + 2.5 mm |
| 5B** | Zn OMADINE ® (0.6%) | POLY-TERGENT ® ADL-ULTRA (2.0%) | NGCA |
| 6A | Zn OMADINE ® (0.6%) | POLY-TERGENT ® ADL-ULTRA (2.0%) | NGCA + 4.5 mm |
| 6B** | Zn OMADINE ® (0.6%) | POLY-TERGENT ® ADL-ULTRA (2.0%) | NGCA |

**Specimen subjected to washing per AATCC 138-1987 before being tested.

EXAMPLE 7

In this example, the procedure of Example 6 was followed to treat two specimens of Nylon 6,6 carpet, with two modifications. First, in lieu of the ADL-ULTRA surfactant, another commercial dye leveling disulfonate surfactant was used, in the same amount, which surfactant is available commercially under the trademark POLY-TERGENT 2A1. The other modification is that washing of the second specimen was not performed in accordance with the AATCC procedure. Rather, the specimen was subjected to a substantially more rigorous hot water washing treatment in an industrial washer using "JO MAP" brand concentrated carpet cleaner detergent in a dilution (JO MAP:Water) of 1:64. The unwashed specimen antimicrobial property result was NGCA+4.5 mm; whereas, the washed specimen exhibited partial growth in the contact area.

EXAMPLE 8

This is a repetition of Example 7, except that the specimen were made of Nylon 6 fibers. The unwashed specimen's antimicrobial property tested at NGCA+2.5; whereas the washed specimen was NGCA.

What is claimed is:

1. A composition for the antimicrobial treatment of fibers and fibrous materials which comprises:

(a) an essentially water-insoluble, antimicrobial compound being zinc pyrithione and (b) a leveling surfactant selected from the group consisting of piperazine-substituted organosulfonates, piperazinone-substituted organosulfonates, and combinations thereof.

2. The composition of claim 1 wherein said zinc pyrithione is present in said composition in an amount of from about 0.001 percent to about 10 percent by weight, based on the weight of the composition.

3. The composition of claim 1 wherein said zinc pyrithione is present in said composition in an amount of from 0.03 percent to about 5.0 percent by weight, based on the weight of the composition.

4. The composition of claim 1 which additionally contains a linear alcohol alkoxylate.

5. The composition of claim 1 wherein said piperazine-substituted organosulfonate is produced by reacting an aralkyl ether sulfonic acid with a piperazine compound selected from the group consisting of 1,2-aminoethyl piperazine, 1,4-piperazinediethane sulfonic acid, anhydrous piperazine, hydrated piperazine, and combinations thereof.

6. The composition of claim 1 wherein said piperazinone-substituted organosulfonate is produced by reacting an aralkyl ether sulfonic acid with a piperazinone compound selected from the group consisting of 4-(2-hydroxyethyl)-2-piperazinone, N,N-dimethyl-2-piperazinone, and combinations thereof.

7. A composition for the antimicrobial treatment of fibers and fibrous materials which comprises:

(a) a zinc salt of a 1-hydroxy-2(1H)-pyridinethione compound represented by the formula

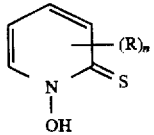

I in which R is a member selected from the group consisting of hydrogen, lower alkyl, lower alkoxy and halogen, and (b) a leveling surfactant selected from the group consisting of piperazine-substituted organosulfonates, piperazinone-substituted organosulfonates, and combinations thereof.

8. The composition of claim 7 wherein piperazine forming said piperazine-substituted organosulfonates is selected from the group consisting of anhydrous piperazine, 1,2-aminoethyl piperazine, 1,4-piperazine-diethane sulfonic acid, hydrated piperazine and mixtures thereof; and piperazinone forming said piperazinone-substituted organosulfonate is selected from the group consisting of a 4-(2-hydroxyethyl)-2-piperazinone, N,N-dimethyl-2-piperazinone, and mixtures thereof.

9. A process for imparting antimicrobial properties to a fibrous material which comprises contacting the fibrous material with an aqueous formulation containing an antimicrobially effective amount of the composition of claim 1.

10. A process for imparting antimicrobial properties to a fibrous material which comprises soaking the fibrous material in an aqueous bath containing an effective amount of the composition of claim 1.

11. The process of claim 10 wherein zinc pyrithione is produced in situ by transchelating a precursor mixture of sodium pyrithione with a water-soluble zinc salt that is additionally present in said aqueous bath.

12. The process of claim 10 wherein the fibers in said fibrous material are polyamide fibers.

13. The process of claim 10 wherein said bath is maintained at about the boiling temperature of the bath, and at a pH form about 5 to about 7.

14. A process for simultaneously dyeing and antimicrobially treating a fibrous material which comprises dipping or spraying said fibrous material with an aqueous bath comprising:
   (a) a water insoluble antimicrobial compound being zinc pyrithione and
   (b) a leveling surfactant selected from the group consisting of piperazinone-substituted organosulfonates, organosulfonates piperazine-substituted organosulfonates, and combinations thereof, and
   (c) an aqueous dye, to provide a dyed fibrous material exhibiting antimicrobial effectiveness against microbes.

15. A process as claimed in claim 14 wherein said fibrous material comprises a carpet of nylon fibers.

16. The process of claim 14 wherein said dye is an acidic dye.

17. The dyed fibrous material product produced by the process of claim 14 exhibiting antimicrobial effectiveness against microbes.

* * * * *